United States Patent

Hydes et al.

[11] 4,203,912
[45] May 20, 1980

[54] COMPOSITIONS CONTAINING PLATINUM

[75] Inventors: Paul C. Hydes; Bernard W. Malerbi, both of Reading, England

[73] Assignee: Johnson, Matthey & Co., Limited, London, England

[21] Appl. No.: 952,607

[22] Filed: Oct. 18, 1978

[30] Foreign Application Priority Data

Oct. 19, 1977 [GB] United Kingdom ............... 43493/77
May 18, 1978 [GB] United Kingdom ............... 20460/78

[51] Int. Cl.² ............................................. C07F 15/00
[52] U.S. Cl. ................................. 260/429 R; 424/287
[58] Field of Search ................................... 260/429 R

[56] References Cited

U.S. PATENT DOCUMENTS

| 3,892,790 | 7/1975 | Tobe et al. | 260/429 R |
| 3,904,663 | 9/1975 | Tobe et al. | 260/429 R |
| 4,115,418 | 9/1978 | Gale et al. | 260/429 R |

OTHER PUBLICATIONS

Connors et al., Platinum Coordination Complexes in Cancer Chemotherapy, Springer-Verlag, N.Y., pp. 13-20, 135 (1974).
Cleare et al., Platinum Metal Rev., 17, 4, 8, 11 (1973).

Primary Examiner—Helen M. S. Sneed
Attorney, Agent, or Firm—Cushman, Darby & Cushman

[57] ABSTRACT

A cis co-ordination compound of platinum having the structure

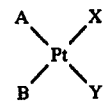

in which X and Y are the same or different ligands selected from sulphate, phosphate, nitrate, tartronate, benzylmalonate, cyclobutane-1, 1-dicarboxylate, phthalate, oxalate, tartrate, pyruvate, gluconate, succinato, glutarato, adipato, pimelato and malato and water and A and B are the same or different alicyclic amines selected from cyclopentamine and cyclohexylamine co-ordinated to the Pt through their N atoms, such that the platinum is present as $Pt^{2+}$.

3 Claims, No Drawings

COMPOSITIONS CONTAINING PLATINUM

This invention relates to platinum co-ordination compounds and to pharmaceutical compositions containing them.

According to a first aspect of the present invention, a composition of matter comprises a cis co-ordination compound of platinum having the structure

in which X and Y are the same or different ligands selected from sulphate, phosphate, nitrate, carboxylate, substituted carboxylate and water and A and B are the same or different alicyclic amines co-ordinated to the Pt through their N atoms, such that the platinum is present as $Pt^{2+}$. By phosphate, we mean both $H_2PO_4^-$ and $HPO_4^{2-}$.

Where X and/or Y is represented by carboxylate or substituted carboxylate, the general formula of which is $CnR_{2n+1}CO_2H$ prefer that n is an integer from 1 to 9 inclusive and that the R groups are the same or different and are selected from hydrogen, substituted or unsubstituted straight- or branched-chain alkyl, aryl, alkaryl, alkenyl, aralkyl, cyclo alkyl and cyclo alkenyl, halogen, pseudohalogen (as hereinafter defined), hydroxy, carbonyl, formyl, nitro, amido, amono, alkoxy, aryloxy and sulphonic acid salts. We intend the above definition also to include oxygen and sulphur, such that one doubly-bonded oxygen or sulphur atom is represented by two R groups and/or Y may also be a dicarboxylate e.g. an oxalate, malonate, tartronate, methylmalonate, ethylnalonate, benzlmalonate, phthalate, sulphate or tartrate.

Where X and Y are both carboxylate, they can together comprise a dicarboxylate bidentate ligand, for example oxalate and ligands having the general formula

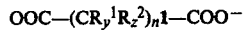

where $n^1$ is an integer from 1 to 6, $R^1$ and $R^2$ are the same or different and are selected from H, lower alkyl, aryl, alkaryl, aralkyl, alkenyl, cycloalkyl, cycloalkenyl, alkoxy, aryloxy, halogen, pseudohalogen, CH, or are combined with the carbon atoms to form a cycloalkyl, cycloalkenyl or an aryl group, and substituted derivatives thereof, and y and z are either 0 or 1 as long as (y+z) is equal to 1 or 2.

One such dicarboxylate ligand is the bidentate malonate ligand which may be substituted or unsubstituted. The malonate ligand may contain substituents selected from the group consisting of lower alkyl, (e.g. methyl, ethyl, n-propyl, isopropyl, n-butyl); aryl, (e.g. phenyl, lower alkyl-, lower alkenyl-, halo-, nitro-, lower alkoxy-substituted phenyl and nephthyl); aralkyl, (e.g. phenylmethyl (benzyl), 2-(1-naphthyl) methyl); alkenyl, (e.g. 4-amino-1-butene, allyl); cyclo-alkyl, (e.g. cycloopropyl, cyclohexyl); cyclo-alkenyl, (e.g. 2-cyclopenten-1-yl), 2-cyclohexen-1-yl); alkoxy; (e.g. methoxy, ethoxy), and hydroxy.

Also suitable are the 1,1-cyclo-alkanedicarboxylic acids, (e.g. 1,1-cyclo-propanedicarboxylic acid, 1,1-cyclobutanedicarboxylic acid) and the 1,1-cycloalkenyldicarboxylic acids, (e.g. 1,1-cyclopropenedicarboxylic acid, 1,1-cyclobutenedicarboxylic acid).

Other suitable dicarboxylate ligands are the succinato, glutarato (pentanedioato), adipato (bexanedioato), pimelato (heptanedioato), malato (cis-buteuedioato) and pinelato (o-benzenedicarboxylate) ligands and these may be either substituted or unsubstituted.

The alicyclic amine has the general formula:

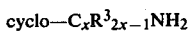

in which we prefer that x is an integer from 3 to 7 inclusive and that the $R^3$ groups are the same or different and are selected from hydrogen, substituted or unsubstituted alkyl, aryl, alkaryl, aralkyl, (alkenyl, cycloalkyl and cycloalkenyl halogen, pseudohalogen (as hereinafter defined), hydroxy, forayl, nitro, alkoxy, aryloxy, amino acylamino, sulphonic acid, sulphonic acid salt, carboxylic acid ester and carboxylic acid salt. Even more preferably all the $R^3$ groups are hydrogen. However, there one or more of the $R^3$ groups is other than hydrogen, it can be a lower alkyl, for example methyl or ethyl, or a solubilizing group, for example a sulphonic acid, carboxylic acid, carboxylic acid salt or a sulphonic acid salt. Where a solubilizing group is used in the formn of a salt, the salt can be, for example, the sodium, potassium or lithium salt, where conditions are appropriate and the clinical conditions require high solubility. We intend the above definition of $R^3$ also to include oxygen and sulphur, such that one doubly-bonded oxygen or sulphur atom is represented by two $R^3$ groups.

Examples of particular compounds according to the invention are the bis(cyclohexylamine) and bis(cyclopentylamine) complexes of platinum (11) with malonate, tartronate (i.e. hydroxymolenate), methylmalonate, ethylmalonate, benzylmalonate, cyclobutane-1,1-dicarboxylate, phthalate, oxalate, sulphate, carboxylate, tartrate, pyruvate and gluconate ligands.

The term "pseudohalogen" in this specification has the meaning given on p.560 of "Advanced Inorganic Chemistry" by Cotton and Wilkinson, Interscience Publishers, 1966, as being "a molecule consisting of more than two electronegative atoms which, in the free state, resembles the halogens; these pseudohalogens give rise to anions which resemble the halide ions in behaviour". Examples of suitable pseudohalogens are cyanide, cyanate, thiocyanate and azide.

The term "cis" as applied to the compounds of the invention indicates that the compounds have planar structure and that A cannot be in a position trans to B and that X cannot be in a position trans to Y.

Normally the compound is used in association with a pharmaceutically acceptable carrier therefor. Accordingly, in a second aspect, the present invention provides a pharmaceutical composition which comprises a compound according to the first aspect of the invention and a pharmaceutically-acceptable carrier for said compound: these compositions can be formulated so as to be suitable, for example, for parenteral or oral administration to animals.

PREPARATION OF PLATINUM COMPLEXES

The following preparative details and results are quoted by way of examples of the preparation of certain specific complexes according to the invention.

EXAMPLE 1  Aquabis (cyclopentylamine) sulphatoplatinum (II)

[Pt(SO$_4$) (C$_5$H$_9$NH$_2$)$_2$H$_2$O]

[PtA$_2$I$_2$] (15g, 0.024 mole) was converted to the solution of the diaquo complex by stirring it together with AgNO$_3$ (8.21g in 25 ml water) at 30°–35° C. for 3 hours. The reaction mixture was filtered through a porosity 4 sinter and the filtrate tested for the absence of Ag$^+$. A saturated solution of sodium sulphate was added to the aquo solution at room temperature, whereupon a white precipitate separated almost immediately. The mixture was stirred and heated to 55° C. and this temperature maintained for half an hour. The product was recovered by filtering the mixture through a porosity 3 sinter, followed by washing on the filter by triturating it with cold water. The solid was dried at 55° C. in vacuo.

Yield = 6.2 g (55%)

This standard reaction, PtA$_2$X$_2$+2Ag$^+$→[PtA$_2$(H$_2$O)$_2$]$^{2+}$, gives a solution referred to as the diaquo complex although it is known to contain a mixture of aquo and hydroxo species.

The complex was recrystallized from a hot solution of 1:1 water and ethanol. Elemental analysis of recrystallized product:

|  | C | H | O | N | S |
|---|---|---|---|---|---|
| Calculated % | 25.15 | 4.65 | 16.76 | 5.56 | 6.72 |
| Found % | 25.27 | 5.01 | 16.28 | 5.82 | 6.43 |

These figures are consistent with the aquo complex with no additional hydration of the molecule.

EXAMPLE 2  cis-bis (cyclopentylamine) bis (chloroacetate)

platinum (II)—[Pt(C$_2$H$_2$O$_2$Cl)$_2$(C$_5$H$_9$NH$_2$)$_2$]

[PtI$_2$A$_2$] (40 g, 0.065 mole) was triturated with water (200 ml) and stirred with thorough trituration at hourly intervals with silver nitrate (21.9 g, 0.129 mole) at 40°–50° C. for 4 hours to form the diaquo complex. The solution thus obtained, after confirming that Ag$^+$ was absent, was mixed with a solution of potassium chloroacetate, which had been prepared by neutralising chloroacetic acid with NOH to pH 6–7. No visible sign of reaction could be seen at first but the solution soon became turbid and rapidly deposited oily droplets which coalesced to a gummy mass. Variation of these and the order of mixing the reactants was tried but failed to prevent formation of the oil. After decanting the supernatant aqueous solution, the residue was set aside to dry and subsequently dissolved in warm ethanol (60° C.). On standing at room temperature, the ethanolic solution deposited white crystals of the chloroacetato complex.

Yield ca. 9.1 g (25%)

Recrystallisation again from hot ethanol yielded clean white crystals which analysed as follows:
Elemental analysis:

|  | C | H | O | N | Cl |
|---|---|---|---|---|---|
| Calculated % | 30.4 | 4.74 | 11.58 | 5.07 | 12.85 |
| Found % | 30.59 | 4.84 | 12.00 | 5.09 | 12.68 |

EXAMPLE 3  Aquabis (cyclopentylamine) phosphatoplatinum (11) [Pt(HPO$_4$)(C$_5$H$_9$NH$_2$)$_2$(H$_2$O)]

cis-[PtI$_2$A$_2$](40 g, 0.065 mole) was converted to the diaquo species by the method of Ex.2 and this solution was allowed to react with an almost saturated solution of Na$_2$HPO$_2$ (20 g, 0.141 mole). The product separated almost immediately as a fine white precipitate, but the mixture was stirred for 2 hours at 30° C. to ensure coordination of the phosphate. After washing with water and acetone the product was vacuum dried.

Yield 11.0 g (37).

Attempts at recrystallisation from hot water, ethanol, DHF and 1:1 ethanol water were unsuccessful, owing to insufficient solubility. Therefore a batch of crude material was submitted for analysis.
Elemental analysis:

|  | C | H | O | N | P |
|---|---|---|---|---|---|
| Found % | 24.30 | 5.45 | 18.70 | 3.87 | 5.64 |
| Calculated for PtA$_2$HPO$_4$2H$_2$O % | 24.13 | 5.47 | 19.30 | 5.63 | 6.23 |

These figures suggest that the complex contains 1 molecule of water of hydration in addition to 1 coordinated water molecule.

Example 4  Bis (cyclopentylamine)malonatoplatinua (II)

[Pt(C$_5$H$_2$O$_4$)(C$_5$H$_9$NH$_2$)$_2$]

cis-[Pt A$_2$ I$_2$] (30 g, 0.048 mole) was added to silver nitrate (16.35 g) dissolved in water (40 ml) and the mixture stirred for 2 hours while the temperature was held at 40° C. After the slurry was filtered (porosity 4 sinter) the filtrate was tested for absence of Ag$^+$ 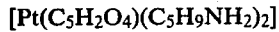 Nalonic acid (8.0 g) was added to this filtrate, which comprises a uo complexes of the amine, and the pH was raised to 7 by adding pellets of solid potassium hydroxide to the warm stirred solution. As the pH reached 5 the clear solution suddenly become cloudy and the product separated as a sticky oil. More alkali was added until pH 7 was reached and the mixture was stirred for 1 hour at 40°–30° C. After cooling to room temperature the mixture was filtered on a porosity 3 sinter yielding 7.5 g of crude product (32% yield).

On recrystallising from hot water, the complex dissolved to the extent of about 1 g in SOOml, giving a good crop of microcrystalline product with the following elemental analysis.
Elemental analysis:

|  | C | H | N | O |
|---|---|---|---|---|
| Calculated % | 33.38 | 5.18 | 5.99 | 13.70 |
| Found % | 33.41 | 5.18 | 6.00 | 13.92 |

Example 5  Bis(cyclopentylamine)tartronatoplatinum (II)

[Pt(C$_3$H$_3$O$_5$)(C$_5$H$_9$NH$_2$)$_2$]

cis-[Pt A$_2$I$_2$](20 g, 0.032 mole) was added in small portions to a well stirred solution of AgNO$_3$ (10.9 g) in water (50 ml). The mixture was stirred for about half an hour and transferred to a porcelain mottar and thoroughly ground up with a pestle. The slurry was returned to a beaker and stirred vigorously whilst keeping the temperature at 40°-50° C. for 3 hours. The tritaration was repeated and the mixture stirred for a further half hour. Finally, after a total reaction time of 4 hours, the mixture was filtered on a porosity 4 sinter. The filter residue was triturated with water and the washings combined with the main filtrate. The total bulk was slurried with charcoal and filtered to give a clear solution.

The filtrate was treated with tartronic acid by adding 5.0 g (0.042 mole) of the solid, stirring until is dissolved, then adding pellets of potassium hydroxide until $pH^2$ was reached. Thereafter the pH was raised gradually by adding a concentrated solution of KOH from a dropper whilst warming and stirring for half an hour. Most of the product had precipitated by the time pH 2.5 had been reached. The reaction mixture was left in a cold room overnight. The product was filtered off on a porosity 3 sinter, washed once with water, air dried in the filter and dried in vacuo at 55° C. for 12 hours.

7.5g of this product was recrystallised from about 1.5 liters of almost boiling water giving 4.13 gram of pure complex (overall yield 29%).

|  | Pt | C | H | N | O |
|---|---|---|---|---|---|
| Calculated % | 40.56 | 32.29 | 5.00 | 5.77 | 16.55 |
| Found % | — | 32.36 | 4.99 | 5.84 | 16.74 |

Clinical testing data

Complexes according to the invention were tested for antitumour activity against either L-1210 leukaemia in mice or S180 ascites. In the results which follow, dosages are quoted in mg/Kg body weight and the evaluation of effectiveness (%T/C) is calculated as the median survival time of treated mice divided by the mediam survival time of untreated (control) mice expressed as a percentrage. Thus a % T/C of 100 indicates no activity and a % T/C of greater than or equal to 125 is considered to be indicative of significant antitumour activity.

(i) Bis(cyclopentylamine)bis(chloroacetato)platinum(II)

Single dose @ 128 mg/kg (L1210) % T/C=100
Daily dose for 9 days @ 32 mg/Kg (S180)% T/C=143

(ii) Bis(cyclopentylamine)tartronatoplatinum(II)

(L1210) % T/C=100

(iii) Bis(cyclopentylammine)malonatoplatinum(II)

(L1210) % T/C=100

(iv) Bis(cyclopentylamine)phosphatoplatinum(II)

(S180) % T/C=120

(v) Bis(cyclopentylamine)sulphateplatinum(II)

(S180) % T/C=130

We claim:

1. A cis co-ordination compound of platinum having the structure

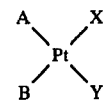

in which X and Y are the same or different ligands selected from sulphate, phosphate, nitrate, tartronate, benzylmalonate, cyclobutane-1, 1-dicarboxylate, phthalate, oxalate, tartrate, pyruvate, gluconate, succinato, glutarato, adipato, pimelato and malato and water and A and B are the same or different alicyclic amines selected from cyclopentamine and cyclohexylamine co-ordinated to the Pt through their N atoms, such that the platinum is present as $Pt^{2+}$.

2. A compound according to claim 1 wherein the phospate is in the form of $H_2PO_4^-$ or $HPO_4^{2-}$.

3. A compound according to claim 1 selected from the group consisting of:
$Pt(SO_4)$ (cyclo $C_5H_9NH_2)_2H_2O$
$Pt(C_2H_2O_2Cl)_2$(cyclo $C_5H_9NH_2)_2$
$Pt(HPO_4)$ (cyclo $C_5H_9HN_2)_2(H_2O)$
$Pt(C_3H_3O_5)$ (cyclo $C_5H_9NH_2)_2$

* * * * *